(12) United States Patent
Fricke et al.

(10) Patent No.: US 9,458,935 B2
(45) Date of Patent: Oct. 4, 2016

(54) LOCKABLE JOINT

(71) Applicants: Helmut Fricke, Meinersen (DE);
Lawrence E. Griffith, Lakeville, MN (US)

(72) Inventors: Helmut Fricke, Meinersen (DE);
Lawrence E. Griffith, Lakeville, MN (US)

( * ) Notice: Subject to any disclaimer, the term of this patent is extended or adjusted under 35 U.S.C. 154(b) by 587 days.

(21) Appl. No.: 13/952,218

(22) Filed: Jul. 26, 2013

(65) Prior Publication Data

US 2015/0010341 A1 Jan. 8, 2015

Related U.S. Application Data

(63) Continuation-in-part of application No. 12/444,158, filed as application No. PCT/EP2007/008582 on Oct. 3, 2007, now abandoned.

(60) Provisional application No. 60/850,090, filed on Oct. 6, 2006, provisional application No. 60/932,127, filed on May 29, 2007, provisional application No. 60/963,699, filed on Jun. 29, 2007.

(51) Int. Cl.
*F16M 11/14* (2006.01)
*F16J 9/26* (2006.01)
*F16J 9/28* (2006.01)
*A61B 17/02* (2006.01)

(52) U.S. Cl.
CPC .............. *F16J 9/26* (2013.01); *A61B 17/0206* (2013.01); *A61B 90/50* (2016.02); *A61B 90/57* (2016.02); *F16J 9/28* (2013.01); *F16M 11/14* (2013.01); *F16M 2200/022* (2013.01); *Y10T 403/32311* (2015.01)

(58) Field of Classification Search
CPC ....... F16C 11/06; F16C 11/10; F16C 11/103; F16C 11/106; Y10T 403/32254; Y10T 403/32262; Y10T 403/32311; Y10T 403/32631; Y10T 403/32688; F16M 11/14; A61B 19/26
See application file for complete search history.

(56) References Cited

U.S. PATENT DOCUMENTS

| | | | | |
|---|---|---|---|---|
| 3,597,780 | A * | 8/1971 | Coyle | F16K 13/06 222/5 |
| 5,020,933 | A * | 6/1991 | Salvestro | A61B 17/02 403/24 |
| 5,201,325 | A * | 4/1993 | McEwen | A61B 17/02 600/202 |
| 5,271,384 | A * | 12/1993 | McEwen | A61B 17/02 248/904 |
| 5,609,565 | A * | 3/1997 | Nakamura | A61B 19/26 248/278.1 |
| 6,379,073 | B1 * | 4/2002 | Yoo | F16C 11/106 248/288.31 |
| 6,491,273 | B2 * | 12/2002 | King | A61B 19/26 248/276.1 |
| 6,632,170 | B1 * | 10/2003 | Bohanan | A61B 19/26 403/83 |

(Continued)

*Primary Examiner* — Daniel Wiley
(74) *Attorney, Agent, or Firm* — Hahn Loeser & Parks LLP; Bret A. Hrivnak

(57) ABSTRACT

A lockable joint such as a lockable ball-and-socket joint comprising a first arm having a swivel head and a socket, the swivel head being pivotably mounted to the socket, and a locking device arranged for locking the swivel head with respect to the socket, the locking device having a piston, a pressure gas source, and an actuating device arranged for reversibly disconnecting the piston from the pressure gas source where in the pressure gas source is a gas cartridge. A seal suitable at a wide range of temperatures and pressures can be used with at least the pressure gas source.

22 Claims, 11 Drawing Sheets

(56) References Cited

U.S. PATENT DOCUMENTS

| | | | |
|---|---|---|---|
| 6,641,323 B2* | 11/2003 | Ronsheim | A16C 11/106 269/25 |
| 6,883,565 B2* | 4/2005 | Marui | F04B 41/02 141/18 |
| 7,160,308 B2* | 1/2007 | Otsuka | A61B 19/26 600/166 |
| 7,341,017 B2* | 3/2008 | Jackson | B63B 17/00 114/343 |
| 7,476,050 B2* | 1/2009 | Ditzler | E02F 9/006 269/25 |
| 2006/0069395 A1* | 3/2006 | Lebet | A61B 17/22012 606/127 |
| 2009/0226243 A1* | 9/2009 | Krywitsky | F16L 27/06 403/38 |
| 2012/0042730 A1* | 2/2012 | Johnson | G01M 7/027 73/579 |
| 2013/0223919 A1* | 8/2013 | Brecht | F16C 11/06 403/31 |

* cited by examiner

LOCKABLE JOINT

This application is a Continuation in Part (CIP) Application of U.S. patent application Ser. No. 12/444,158 filed Apr. 2, 2009, which is a national stage application of PCT/EP2007/008582 filed Oct. 3, 2007, and claims priority to and the benefit of U.S. provisional patent application 60/850,090, filed Oct. 6, 2006, U.S. provisional patent application 60/932,127, filed May 29, 2007, and U.S. provisional patent application 60/963,699, filed Jun. 29, 2007, which are incorporated herein by reference.

BACKGROUND AND SUMMARY

The invention relates generally to the field of surgical instrumentation. More particularly, the invention relates to a lockable joint and a seal for use in conjunction with a lockable joint, especially a lockable ball-and-socket joint including a locking device having a piston, a pressure gas source, and an actuating device arranged for reversibly disconnecting the piston from the pressure gas source, these components including one or more high pressure seals. Such seals can relate especially to a high pressure gas seal for use in medical systems, the seal made at least in part of a material being resistant to a sudden drop in gas pressure, the material further having substantially stable performance at pressures between the high pressure and the low pressure, the material further having substantially stable performance below a low temperature and above a high temperature, and the material further having low porosity.

A lockable joint is known from U.S. Pat. No. 5,201,325. The lockable joint in this document can be actuated by pressured air that is delivered via a gas hose. As the gas pressure of pressurized gas in gas hoses usually is not sufficient to clamp the lockable joint safely, a pressure enhancing system is provided. Another lockable joint is known from U.S. Pat. No. 5,271,384. This lockable joint suffers from a clamping force that is not sufficient for many applications.

It is the problem of the present invention to mitigate problems associated with lockable joints known from prior art, and to provide seals capable of operating with and releasing high gas pressure.

The invention solves the problem with a lockable joint and a seal for a lockable joint, especially a lockable ball-and-socket joint that can include a locking device having a piston, a pressure gas source, an actuating device arranged for reversibly disconnecting the piston from the pressure gas source where the pressure gas source is a gas cartridge, and one or more seals facilitating the retention of gas between components. The problem of managing the gas pressure is solved according to specialized seals, especially seals for use in high-pressure gas-actuated medical systems, the seal made at least in part of a material being resistant to a sudden drop in gas pressure from a high pressure, e.g. more than 4 MPa (40 bar) to a low pressure, e.g. less than 0.11 MPa (1.1 bar), the material further having substantially stable performance at pressures between the high pressure and the low pressure, the material further having substantially stable performance below a low temperature, e.g. in particular embodiments, below −5° Celsius, or below −10° Celsius, or below −50° Celsius, and above a high temperature, e.g. in particular embodiments above 100° Celsius, or above 110° Celsius, or above 130° Celsius, and the material further having low porosity.

According to another aspect, there can be a method for making a seal for use in high pressure gas medical systems, comprising receiving a low-porosity material having a resistance to a sudden drop in gas pressure from a high pressure, e.g. more than 4 MPa (40 bar) to a low pressure, e.g. 0.11 MPa (1.1 bar), the material further having substantially stable performance at pressures between the high pressure and the low pressure, the material further having substantially stable performance below −5° Celsius, and in particular embodiments below −10° Celsius, and in other embodiments below −50° Celsius, and the material having substantially stable performance above 100° Celsius, and in particular embodiments above 110° Celsius, and in other embodiments above 130° Celsius. The method can further include forming a seal from the received material.

Usually, surgical retractors were hand-held instruments with multiple curved fingers used to hold open incisions during surgical procedures. The surgeon or an assistant would hook the fingers of the surgical retractor over the edge of an incision and apply tension to hold the incision open to provide access for the surgeon to internal bodily structures.

In approximately the last two decades, surgical retractors have been developed that are secured to a surgical table or other structure to allow retraction to be accomplished without the necessity of the surgeon or an assistant constantly holding the retractor.

For surgical retractors system according to the invention, a table rail post may be the foundation of a surgical retractor system. It provides an anchor for a frameset and other hardware onto which retractor instruments and other surgical instruments may be attached. A variety of retractor instruments with variably shaped retractor fingers are used in surgery to assist the surgeon in holding a surgical incision open or to move anatomical structures out of the way. The surgical retractor systems may use cam mechanisms or occasionally screw clamps to lock various members of the retractor system in position.

The surgical retractor system according to the invention may be a round stock retractor system and/or flat stock retractor system. Flat stock retractor systems suffer the limitation that because of the rectilinear nature of the various components, the components must be joined at substantially right angles in order to interconnect. Thus, the number of orientations in which flat stock retractor systems can be assembled is limited.

Round stock retractor systems generally are preferred because they allow for the interconnection of the various retractor system components at a variety of different angles because of the ability of the round stock parts of the system to rotate relative to one another and to clamp components.

Round stock retractor systems include various rod shaped parts that, initially, are connected together by screw-threaded type clamps. When screw-threaded type clamps are used, there might be a tendency for the screw clamps to deform the cylindrical members of the retractor system. Further, setting up, positioning and interconnecting the parts of the retractor system can require both hands, or possibly both hands of one individual, plus an assistant to assemble the system. Thus, cam lock or over center lock connection systems are preferred for mounting the surgical retractor to the first arm and/or for fixing the anchor element to the third arm.

The cam lock system may include two interconnected clamps that are configured to grip the rod shape retractor system members and that can be adjusted in rotation relative to each other. One rod shaped component is gripped in each clamp. The two interconnected clamps are activated by some sort of actuator such as a lever which then locks the two clamps to two rod-shaped members and also simultaneously locks the two clamps relative to each other in rotation. One disadvantage of this arrangement is that when the clamps are released, they are released completely from both rod-shaped members as well as in relative rotation, requiring that the retractor system be completely repositioned and realigned before re-clamping.

Surgical retractor systems are used to manipulate living tissue. The application of pressure to living tissue can damage cell structure or reduce blood flow to the tissue. Living tissue can be damaged by the application of pressure for too long a time. Therefore, it is recommended that during surgical procedures where mechanical retractors are used, periodically the retractors should be loosened or tension should be lessened on the retractors to allow increased blood flow to the tissue being retracted to prevent tissue hypoxia and possible necrosis. This requirement, along with the limitation of current retractor systems, creates a dilemma for the surgical team. The surgical teams can disconnect the surgical retraction system periodically but then be required to make complete adjustments of each surgical retractor to reconnect it. Alternately, the surgical team can leave the living tissue retracted under tension for long periods of time and risk tissue damage or necrosis to the tissues being retracted. Surgical team members tend to be reluctant to disconnect and then readjust the retractor system if the readjustment is time consuming or unwieldy or if readjustment will alter the carefully positioned relationship of anatomical structures.

Another issue that arises with current round stock surgical retractor systems arises from the fact that surgeons generally prefer to locate retractors so that they are providing retractive tension at an angle. Surgeons prefer this approach in order to move the retractor to one side of the field in which they must work so that the retractor does not interfere with their movements. When the surgical retractors are offset, quite often it is impossible to position the retractors so that the retractor is pulling completely linearly with relation to the long axis of the rod-shaped members. This imparts a torsional or rotational force to the clamps that are secured to cylindrical or rod shaped members of the retraction system. This force tends to cause the clamps of the retraction system to slip about the rods in a rotational fashion. A common response to this problem is to increasingly tighten the clamp that is applied to the rod-shaped member. Unfortunately, when tightened beyond a certain point, the clamp will tend to create deformation or galling of the rod shaped member to which it is clamped making it more difficult to adjust the system for future usage.

A problem that arises with currently available retraction systems is that when a retractor is fixed to the system by a current clamp the multi-axis joint created between components is completely locked so that the components joined are immovably fixed in all axes. Commonly, it is necessary for the surgeon or an assistant to increase or readjust retractions for certain activities. Adjusting retractions means that the surgeon or an assistant must loosen the clamp holding the retractor, reposition the retractor, and then reapply the clamp. Since prior art clamp releases completely from two rods and in rotation simultaneously, at least two hands are required to realign and retighten the system. This can be quite awkward as there is a period of time where tension on the retractor is reduced and tissues may move in an undesirable fashion when the tension is reduced.

Retractor frames generally include a first frame arm, a second frame arm and a locking device that may also be called clamping member and that secures the left frame arm and the right frame arm in a fixed position, so that a surgical retractor may secured to the left and right frame arms. In addition, retractor frames generally include a third support arm which can be secured to a surgical table rail post. Existing retractor frames suffer a number of limitations. For example, the clamping member that secures the right and left frame arms generally locks the right and left frame arms in position simultaneously. While convenient locking, the frame arms simultaneously can make it difficult to adjust the right and left frame arms independently of one another. In addition, in many prior art retractor frames the clamping member also secures the pivotable connection between the support arm and the clamping member at the same time that the right and left frame arms are secured, sometimes making it difficult to adjust the retractor frame as desired.

For the purpose of the following description a locking device may be any device that is arranged and adapted for immobilizing the swivel head relative to the socket. It is possible to provide two or even more locking devices. The locking device may provide a frictional locking with the swivel head. Alternatively, the locking device may be adapted for a positive locking or for a combination of both positive and frictional locking.

The actuating device may be any device that is adapted and arranged for allowing and interrupting a gas communication between the gas cartridge and the piston. For example, the actuating device may be a valve.

A gas cartridge may be a cartridge that contains a chemical composition or mixture of chemical compositions that is/are gaseous at ambient temperature of 20° C. and ambient air pressure of 1013 hPa. Alternatively, the gas cartridge contains a chemical composition that may be brought into contact with another chemical composition to react chemically so that such a gas is produced.

It is an advantage of the present invention that it is not necessary to provide an external source of pressurized air. Such an external source of pressurized air may not be available. Especially in hospitals, pressurized air systems are often contaminated with bacteria, so that this air must not be used for operation devices. As a further advantage, air hoses are no longer needed. Air hoses bear the risk of bursting and have to be checked regularly. They are also inconvenient to use and bear the risk of stumbling for personnel. It is another advantage that the gas cartridge may be a disposable gas cartridge. Disposable gas cartridges are easy to handle and to store, so that the lockable joint has a high reliability and availability. It is another advantage that the lockable joint can be actuated easily. A lockable joint is therefore advantageous for high precision applications.

In a preferred embodiment, that gas cartridge has an internal pressure of more than 4 MPa or 40 bar. In particular, the internal pressure is more than 5 MPa or 50 bar. This high pressure makes it possible to actuate the locking device directly by the piston. Standard air pressure systems used e.g. in hospitals usually have a pressure of below 0.7 MPa, so that the force of the piston has to be increased by a suitable device. These devices are error-prone and expensive. The use of a gas cartridge having an internal pressure of more than 4 PMa thus leads a lockable joint that is easy to manufacture, cheap and robust.

In a preferred embodiment, the gas cartridge contains less than 1000 g of gas. In particular, the gas cartridge contains less than 100 g of gas, e.g. 12 g to 50 g of gas. These kinds of gas cartridges are small and easy to handle, but contain a sufficient amount of gas for most applications of the lockable joint.

It is preferred that the gas cartridge contains carbon dioxide, pressurized air, pressurized nitrogen, pressurized nitrous oxide, pressurized noble gas, pressurized oxygen, or a mixture of two, three, four or five of the aforementioned substances. In particular, it is preferred that the gas cartridge contains carbon dioxide and may therefore be called a carbon dioxide cartridge. Carbon dioxide is non-toxic, easy to manufacture and harmless to handle. It is an advantage, that carbon dioxide is a liquid at room temperature of 20° C., if the pressure is above 5.8 MPa. As a liquid, carbon dioxide has a high density so that even small carbon dioxide cartridge can store a significant amount of carbon dioxide.

It is preferred that the carbon dioxide cartridge contains sterile carbon dioxide. Used carbon dioxide from a sterile carbon dioxide cartridge may be released into the ambient air even in an operating room.

Seals used with the gas cartridge, conduits directly or indirectly to the gas cartridge, the actuating device, and/or other components, are designed to withstand high-pressure gases and various operating environments used in conjunction with or related to aspects herein.

It is preferred that the lockable joint has a main body, the main body comprising the socket in the locking device, the locking device having a fixing element that is received in the main body, and the piston being arranged for pressing the fixing element against the swivel head. It is particularly advantageous that the piston and the fixing element are connected, such that moving the piston in a piston working direction leads to movement of the fixing element in a fixing working direction, whereby the piston working direction is parallel to the fixing element working direction. This yields a particularly advantageous flux of force.

It is a particular advantage if the piston and the fixing element are directly coupled, such that moving the piston by pre-determined pistons leads to a movement of the fixing element by the same pre-determined distance. That is, no force increasing mechanism is required. That leads to an easy to manufacture lockable joint. In particular, the piston is arranged for pressing against the swivel head. The contacting part may be called fixing section.

In an preferred embodiment, the main body comprises a cylinder, the cylinder having an inlet opening, the piston being moveably received in the cylinder and comprising a fixing section for pressing against the swivel head, the fixing section being located opposite the inlet opening. In this embodiment, gas streaming thru the inlet opening into the cylinder pushes the piston towards the swivel head thus pressing its fixing section against it. The socket is arranged such that the swivel head presses against the socket when the fixing section presses against the swivel head. Thus, the swivel head is locked between the socket and the fixing section. As the piston is snugly received in the cylinder and as the socket is rigidly mounted to the main body, the swivel head is locked, i.e. tightly fixed and clamped, to the main body. If a high gas pressure is provided, e.g. 6 MPa, a clamping force of more than 4000 N is easily achievable.

In a preferred embodiment, the main body comprises a gas cartridge retainer for changeably receiving the gas cartridge. It is then possible to use disposable or one-way gas cartridges that are easily available at low prices. Further, it is possible to use the lockable joint in places where a pressurized air system is not available. Examples are developing countries or remote places.

It is preferred that the fixing element, in particular the fixing section of a piston, is arranged for contacting the swivel head in a fixing element contact area that is a ring-shaped and has a ring width of less than 1 mm. This yields a particularly strong clamping force that the locking device exerts on the swivel head, as a small ring width leads to a high pressure that in turn causes an elastic deformation of the swivel head.

In a preferred embodiment, the fixing element is arranged for frictional locking between the fixing element and the swivel head. This leads to an easy to manufacture and robust lockable joint. The contact section area may be segmented. To achieve this, the fixing element, e.g. the fixing section of the piston, may be provided with clearances or cuts. These clearances may also be arranged to enable cleaning or the lockable joint, in particular the swivel head, after use or to disinfect the lockable joint.

It is preferred that the swivel head has swivel head outer diameter and contacts the fixing element, e.g. the fixing section of the piston, in a ring-shaped swivel head contact area that is larger than 0.94 times the swivel head outer diameter.

It is preferred that the first arm has an arm longitudinal axis and the contact area outer diameter and the arm longitudinal axis form a substantially constant effective angle of less than 20°. In particular, it is preferred that the effective angle is larger than 1°.

To allow for as many lock-and-release cycles, it is preferred that the gas cartridge has a gas cartridge outlet opening, the cylinder and a gas cartridge being in gas communication via a gas conduct between the gas cartridge outlet opening and the cylinder inlet opening, wherein the gas conduct has an volume of less than 1000 mm$^3$, in particular less than 500 mm$^3$. To maximize the number of lock-and-release cycles, it is also preferred that the piston has a stroke of less than 2 mm, and in particular less than 1 mm.

To provide for a strong clamping force, the piston preferably has a piston diameter of more than 20 mm.

According to another aspect, the invention relates to a lockable joint assembly that comprises (a) a lockable joint according to the first aspect of the invention, (b) a second arm having a second swivel head, (c) a second socket head being pivotably mounted to the second socket, (d) a second locking device arranged for locking the second swivel head with respect to the second socket, the second locking device having (i) a second piston disconnectably connected to the gas cartridge and (ii) a second actuating device arranged for reversibly disconnecting the second piston from the gas cartridge. For the sake of easy handling, the second arm is preferably arranged opposite the first arm.

To fix the lockable joint to an anchor element, the lockable joint preferably comprises (a) a support arm having a support swivel head, (b) a support arm socket, pivotably mounted to the support arm socket, and (c) a support arm locking device arranged for locking the support arm swivel head relative to the support arm socket, the support arm locking device having (i) a support arm piston interruptibly connected to the gas cartridge and (ii) a support arm actuating device arranged for reversibly disconnecting the support arm piston from the gas cartridge.

According to still a further aspect, the invention relates to a surgical retractor system, comprising (a) a lockable joint assembly according to the invention, (b) an anchor element adapted for mounting to an operating table, the anchor element being releasable mounted to the support arm, the first arm being adapted to act as a frame element for receiving at least one surgical retractor.

The surgical retractor frame of the present invention is adapted to be anchored to a surgical post secured to a surgical table rail, or to another fixed structure, to allow the application of surgical retractors that are used for the retraction of anatomical structures.

The surgical retractor frame of the present invention may include a main body in form of a control hand piece, a support arm and two frame arms, i.e. the first arm and the second arm.

The support arm and two frame arms (first arm and second arm) can be articulated with the control hand piece via ball joints. Each ball joint supports one of the support arms and the two frame arms. Each ball joint is independent lockable and releasable at any location within its articular range. That is, each ball joint can be independently released, adjusted and secured independent of the other two ball joints.

The independent gas pressure driven locking mechanism of the present invention is operated by a pressurized gas source in form of gas cartridge, e.g. a small pressurized gas cylinder containing pressurized gas such as carbon dioxide, nitrogen, or compressed air.

In one exemplary embodiment, the pressurized gas supply is provided in a small carbon dioxide cartridge or cylinder. The carbon dioxide cartridge is contained within the control hand piece of the present invention. The carbon dioxide cylinder is intended to be replaced with each use of the surgical retractor frame. For example, the control hand piece may have a generally cylindrical chamber into which the compressed gas cylinder may be placed. Once the gas cylinder is placed in the chamber, a screw for carding the gas cylinder may be inserted behind the gas cylinder and tightened until the gas cylinder is pierced by a trocar or hollow needle. The gas cylinder is simultaneously sealed to the control hand piece.

The main body or control hand piece may further include an independent push button or other valve actuator to operate each individual spherical ball joint. The support arm locking device operates the ball joint for the support arm.

In one aspect of the invention, the operation of the support arm locking device is such that the support arm is locked by pressurized gas pressing the support arm piston against the swivel head, i.e. a spherical member, of the ball joint except when the actuating device, e.g. a push button, is depressed. The support arm locking device is structured such that when its push button is depressed, pressurized gas acting against the support arm piston is released while pressurized gas is sealed off within the gas cartridge so that gas is not vented constantly. The actuating device for the first arm operates the first arm, i.e. the right frame arm, and the second locking device operates the second arm, i.e. the left frame arm. The ball joints are arranged so that some tension is kept on the spherical member by the piston, even when the gas pressure is released. This provides tension so that the frame arm may be adjusted into a desired position without "flopping" in response to gravity.

In one aspect of the invention, the pressurized gas cylinder has a fail-safe pressing release so that if a hospital staffer mistakenly places the surgical retractor frame in an autoclave for sterilization with the gas cylinder still installed, the gas cylinder will vent safely, thus preventing the risk of an explosion in the autoclave.

In one aspect of the invention, the pistons which bear with their fixing sections against the ball joint spheres have a piston seal including a stainless steel spring within the piston seal. O-rings or pistons without seals may also be utilized.

In a preferred embodiment, the seal(s) (or O-rings) are high pressure gas seal(s) made at least in part of a material having a resistance to a sudden drop in gas pressure, the material further having substantially stable performance at pressures between a low pressure and a high pressure, the material further having substantially stable performance below a low temperature and above a high temperature, and the material further having low porosity.

The compressed gas that is used to operate the pistons in the surgical refractor frame may be supplied at a pressure between about 200 and 350 pounds per square inch. In one aspect of the invention, the system operates at pressures of roughly 300 pounds per square inch.

It is notable that the piston travel in the surgical retractor frame may be very short; on the order of less than one millimeter. The fit of the piston within the cylinder is quite tight so that the piston maintains tension on the sphere of the ball joint even when the pressure on the piston is released. The piston and sphere of the ball joint may be made of a metallic material such as, for example, Nitronic 60, Galltough™, or V4A™ steel.

The locking devices may comprise dual function push button valves that both vent pressure from the respective piston and cylinder and seal the gas passages or ducts from the pressurized gas source simultaneously.

The control hand piece may include an ergonomic hand grip. The body of the control hand piece may be formed of, for example, stainless steel such as 400 series stainless steel or V4A steel.

In one embodiment of the invention, the first and second, e.g. the left and right, frame arms and the support arm may be tubular structures rather than the more conventional solid bars. This lightens the structure of the surgical retractor frame without significantly sacrificing strength. The spheres of the ball joints may be solid or hollow. All of the metallic parts of the present invention may also be formed of materials such as titanium or stainless steel.

The gas cartridge may be supplied in a sterile or a non-sterile state. When non-sterile cartridges are used, a sterile sleeve may be used to maintain a sterile field in the operating room to allow for cartridge exchange, if needed, during a surgical procedure.

BRIEF DESCRIPTION OF THE DRAWINGS

Preferred embodiments are now described with respect to the drawing, in which

FIG. 3b is a schematic cross sectional view of a detail of FIG. 3a;

FIG. 4b is a second front cross sectional view of the embodiment of FIG. 4a;

FIG. 5b is a side cross sectional view of the piston of FIG. 5a;

FIG. 6b a cross sectional view of the socket of FIG. 6a;

DETAILED DESCRIPTION OF THE DRAWINGS

Figure 1:
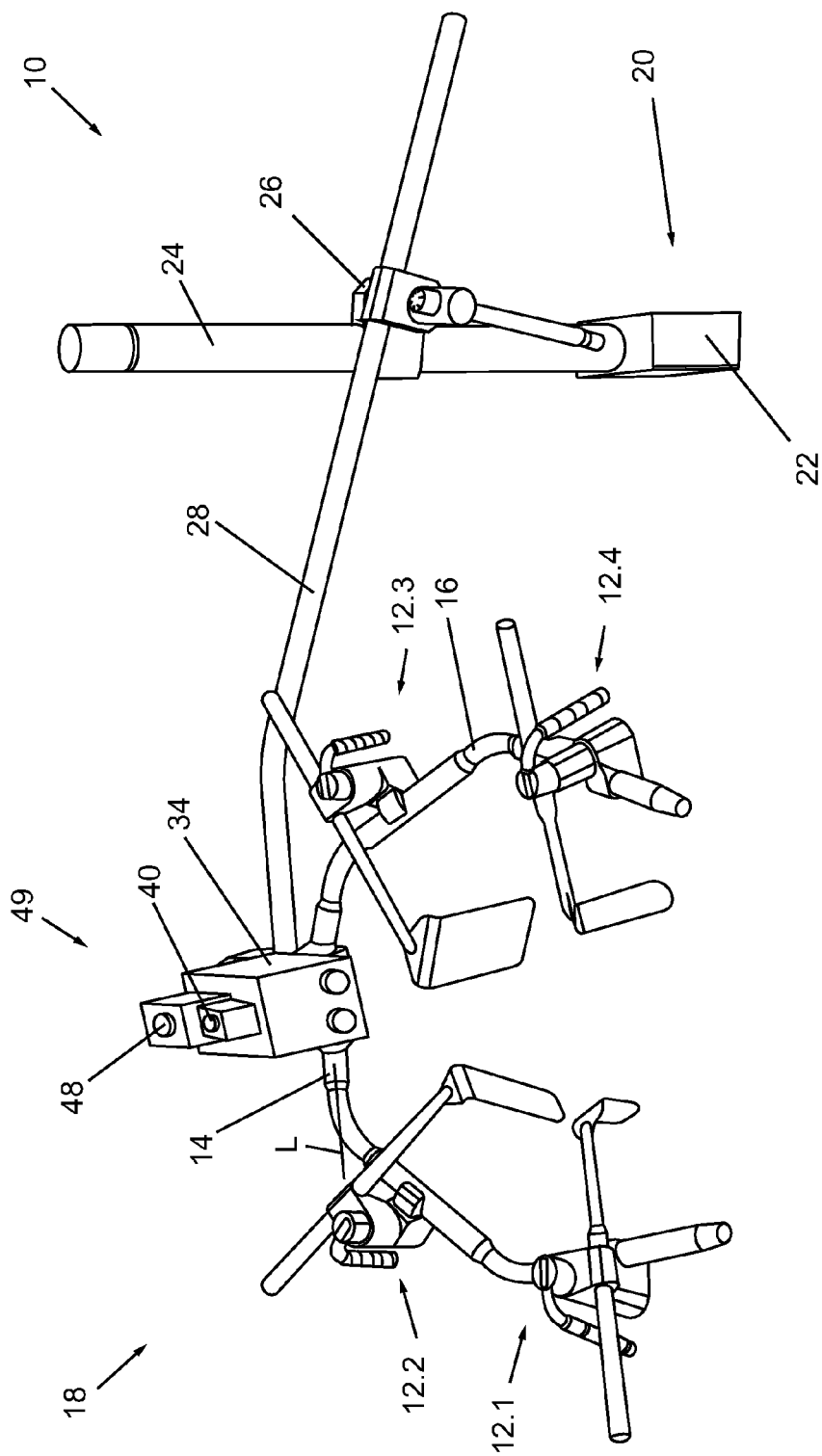
FIG. 1 is a perspective view of an exemplary embodiment of a surgical retractor system according to the present invention.

FIG. 1 shows a surgical retractor system 10 comprising four surgical retractors 12.1, 12.2, 12.3 and 12.4. In the following, reference numerals without counting suffix refer to the object as such. Surgical retractors 12 are mechanically clamped either to a first arm 14 or a second arm 16 of a surgical retractor frame 18.

The surgical retractor frame 18 also comprises an anchor element 20 that is adapted for mounting to an operating table (not shown). Anchor element 20 has a coupling anchor 22 that is connected to a clamping rod 24. An anchor element joint 26 is provided to releasably and pivotably mount a support arm 28 of the surgical retractor frame 18. First arm 14 and second arm 16 have the same shape and are sectionwise cylindrical and form a bow. Support arm 28, first arm 14, second arm 16 and a schematically shown main body 34 (described below in greater detail) linking them to each other are parts of a lockable joint assembly 49 (also described below in greater detail).

Figure 2:
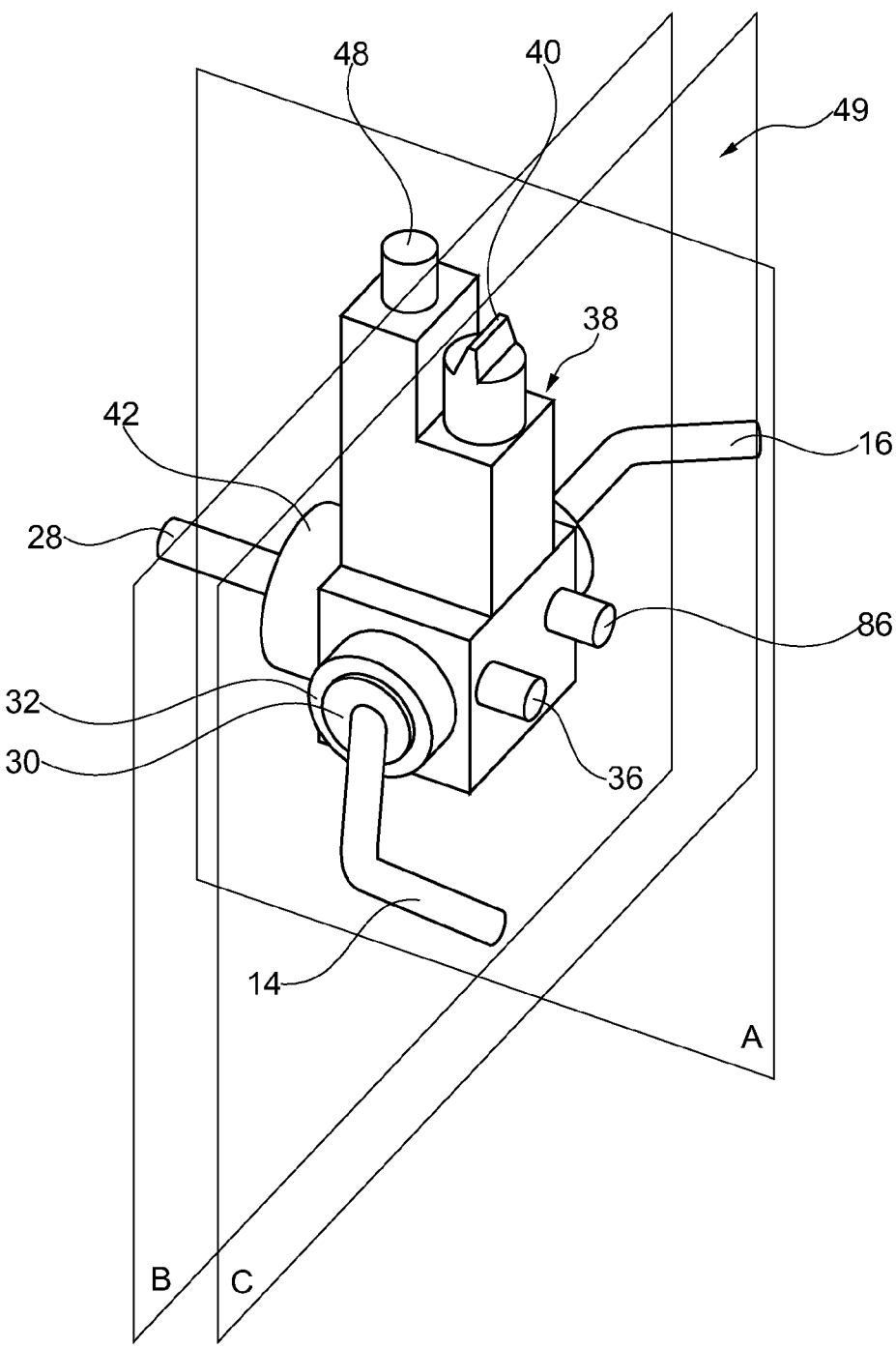
FIG. 2 is a perspective view of an exemplary embodiment of a lockable joint assembly according to the present invention.

FIG. 2 depicts lockable joint assembly 49. First arm 14 has a swivel head 30 that is received in a socket 32. Socket 32 is part of main body 34 that may also be called a control hand piece. Main body 34 comprises a push button 36 of a locking device that comprises components that are used to lock or release first arm 14 to main body 34 and will be described in greater detail below. Main body or control hand piece 34 also comprises a gas cartridge retainer 38 that has a gas cartridge chamber screw 40, which is arranged releasably. FIG. 2 also depicts a support arm socket 42 that is also part of main body 34.

Figure 3A:
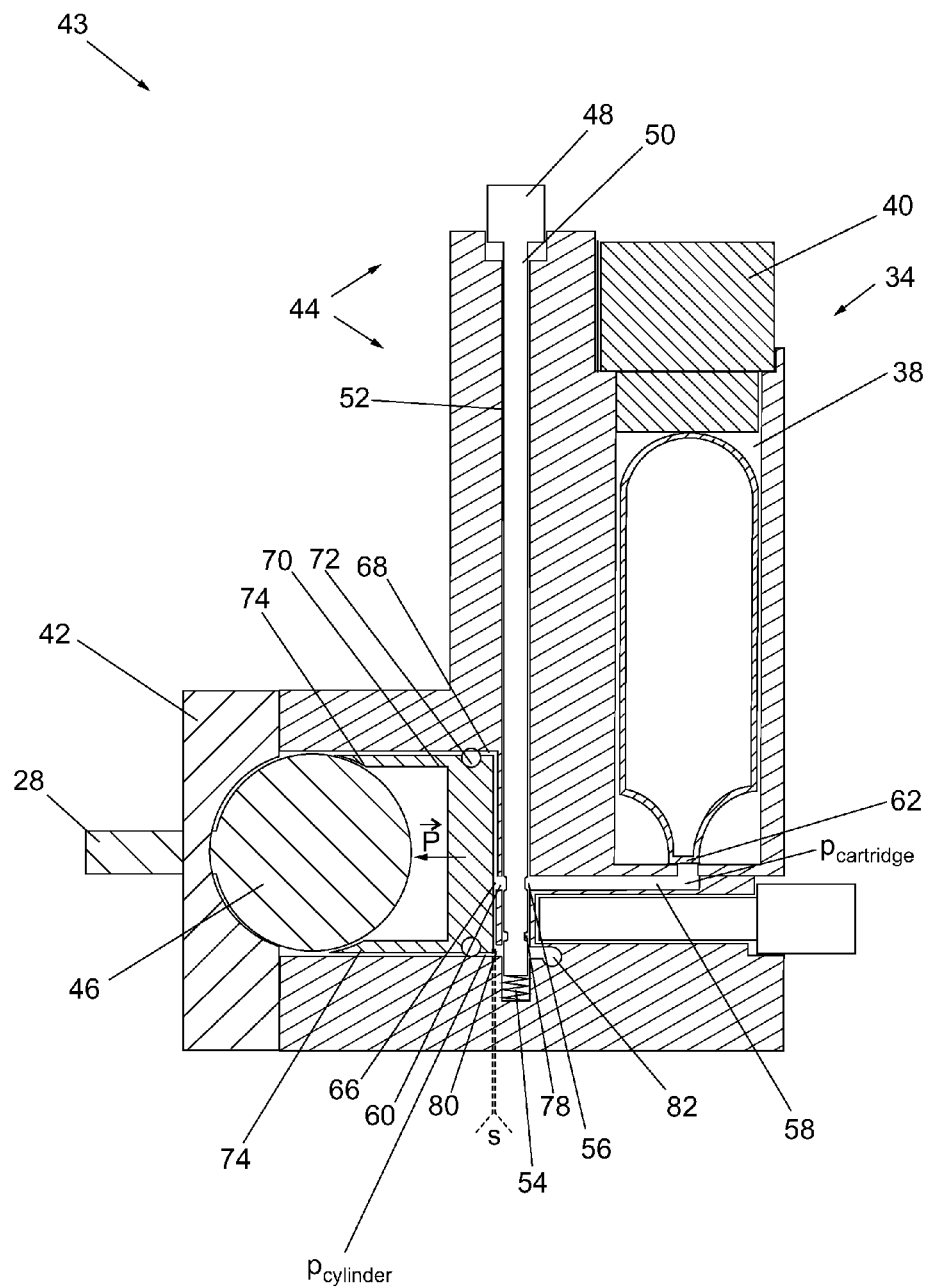
FIG. 3a is a side cross sectional view according to plane A of the embodiment depicted in FIG. 2 in a locking position including the present seal.

FIG. 3a shows a sectional view of a lockable joint 43 according to the invention. At the same time, FIG. 3a depicts a cross section of lockable joint assembly 49 with respect to plane A of FIG. 2. It is to be noted that a lockable joint 43 by definition has only one arm and one joint, especially one ball joint. Devices with more than one arm are referred to as lockable joint assemblies. Preferably, all arms of the lockable joint assembly are mounted to one single rigid main body. Thus, a lockable joint 43 is part of lockable joint assembly 49.

In FIG. 3a a support arm locking device 44 is depicted that is adapted for releasably locking a support arm swivel head 46 of support arm 28 to main body or control hand piece 34. Support arm locking device 44 comprises a support arm push bottom 48 that protrudes over main body 34, such that at it can be easily actuated by finger tip. Alternatively, support arm push button 48 may be completely located in a recess, so that it is protected against unintended actuation.

Support arm locking device 44 also comprises a support arm valve member 50 that has a substantially cylindrical shape and is snugly received in bore 52 and sealed in a gas-tight against it. Support arm valve member 50 is mounted to support arm push button 48 and is pre-tensioned in a locking position (shown in FIG. 3a) by a spring 54 located opposite the support arm push button 48.

In the locking position, an annular recess 56 in support arm valve member 50 provides gas communication of a first gas channel 58 to a second gas channel 60 that both have a diameter of 3 mm. Annular recess 56, first gas channel 58, and second gas channel 60 form a gas duct 61 having a volume V. This volume V should be reasonably small, e.g. 250 mm³ or less. However, a larger volume V is possible as well. First gas channel 58 may and extends from bore 52 to gas cartridge retainer 38 and in particular to a gas cartridge outlet opening 62 of a carbon dioxide cartridge 64. Carbon dioxide cartridge 64 may be disinfected e.g. by x-ray or γ-ray exposure.

Carbon dioxide cartridge 64 contains about 12 grams of carbon dioxide at a pressure $p_{cartridge}$ of about 6 MPa. At room temperature, most of the carbon dioxide is liquid due to the high pressure. Carbon dioxide escapes from carbon dioxide cartridge 64 through first gas channel 58, annular recess 56, and second gas channel 60 and streams through a cylinder inlet opening 66 into a cylinder 68. In cylinder 68, a support arm piston 70 is received and sealed in gas-tight manner via an seal 72, such as an o-ring. Alternatively, a gasket, washer, or other seal may be used.

In the locking position shown in FIG. 3a, a gas pressure $p_{cylinder}$ in c cylinder 68 equals to the gas pressure $p_{cartridge}$ in carbon dioxide cartridge 64. Thus, piston 70 is pressed in a piston working direction $\vec{P}$ so that a fixing section 74 of cylinder 68 that acts as a fixing element is pressed against support arm swivel head 46. In other words, piston 70 presses directly against the swivel head. In FIG. 3a, the piston working direction $\vec{P}$ is equal to a fixing element working direction. The distance between a locking position of support arm piston 70 and a position in which it is completely retracted, i.e. in which it abuts the wall with cylinder inlet opening 66, is called stroke s. In other words, stroke s is the maximum piston travel. It equals 0.5 mm.

Figure 3B:
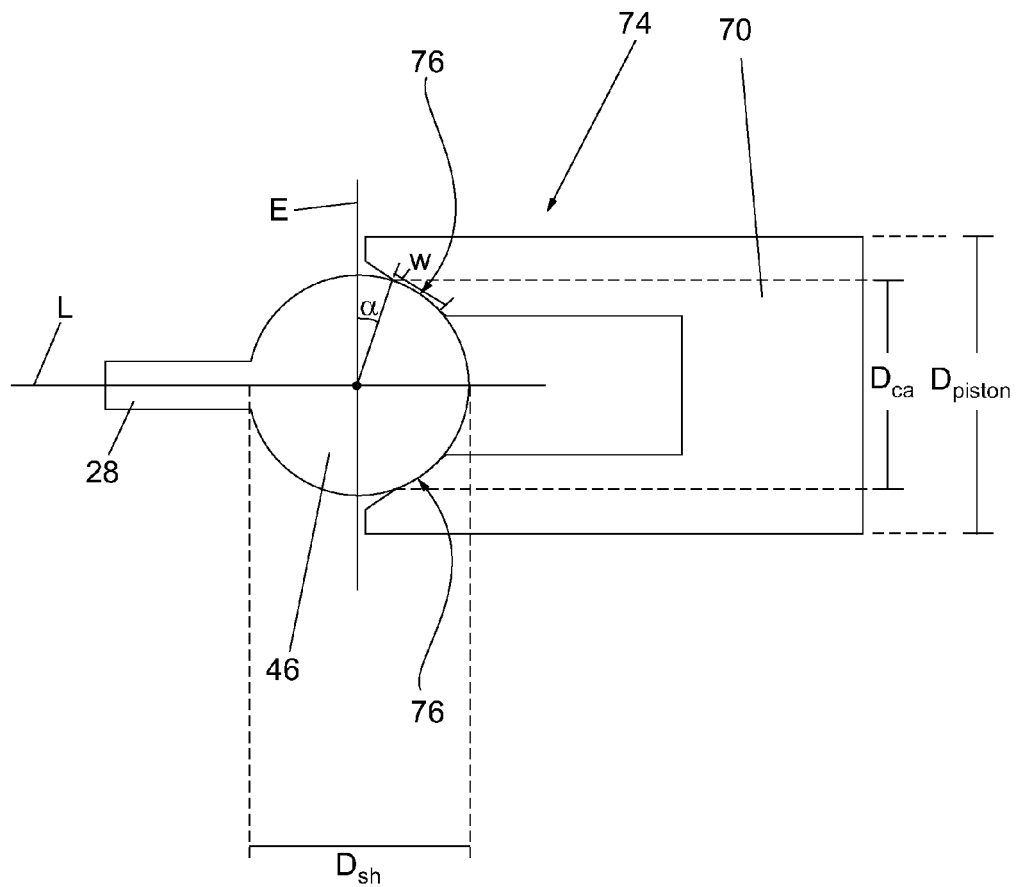

FIG. 3b shows a schematic cross section of support arm piston 70 and support arm swivel head 46. The fixing element in form of fixing section 74 contacts the support arm swivel head 46 in a fixing element contact area 76. The fixing element contact area 76 is ring-shaped and has a ring width w of about 0.5 mm. The surfaces of support arm swivel head 46 and fixing section 74 are polished or grinded so that a frictional locking is provided. Support arm swivel head 46 is a ball or a sphere and has a swivel head outer diameter $D_{sh}$. Support arm piston 70 has a diameter $D_{piston}$, that is 0.94 times the swivel head of the diameter $D_{sh}$ or larger. Contact area 76 has a contact area outer diameter $D_{ca}$ that 0.94 times the swivel head of the diameter $D_{sh}$ or larger.

Support arm 28 has a longitudinal axis L. If longitudinal axis L is aligned with the longitudinal axis of support arm piston 70, as shown in FIG. 3b, an effective angle α is formed between a plane E perpendicular to longitudinal axis L and contact area outer diameter $D_{ca}$.

Figure 3C:
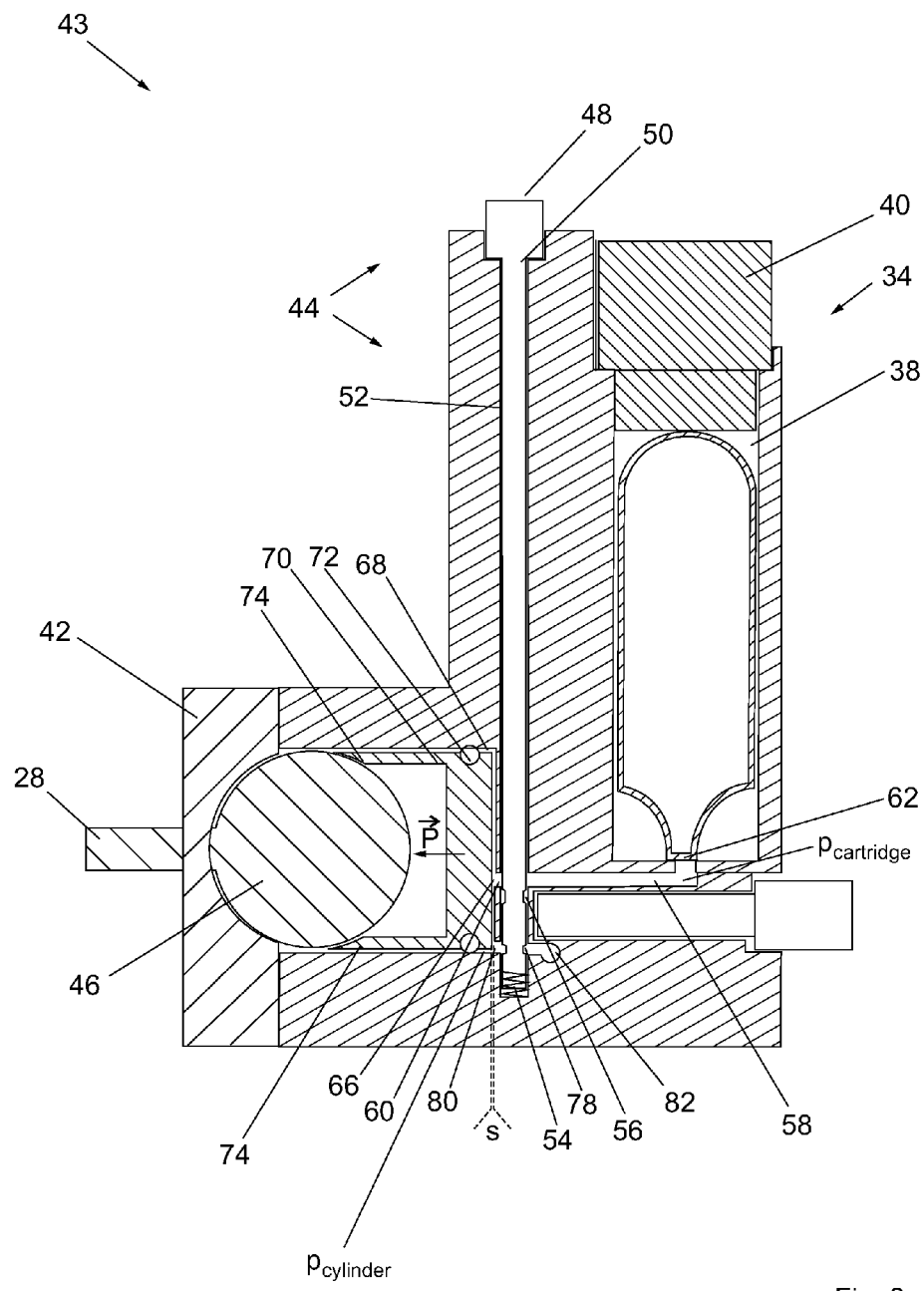
FIG. 3c is a view according to FIG. 3a depicting a release position including the present seal.

FIG. 3c shows support arm locking device 44 in its release position with support arm push button 48 pushed down against the biasing force of spring 54. It can be seen that annular recess 56 no longer links first gas channel 58 to second gas channel 60 thus interrupting cylinder 68 from carbon dioxide cartridge 64. In the release position, a second annular recess 78 connects a first outlet channel 80 to a second outlet channel 82 that leads to an exhaust opening (not shown). Thus, in the release position, carbon dioxide escapes through first outlet channel 80, second annular recess 78, and second outlet channel 82 until the gas pressure $p_{cylinder}$ in cylinder 68 equals the ambient air pressure $p_{ambient}$. Support arm swivel head 46 may now be pivoted freely with respect to main body 34.

In embodiments such as shown in the figures (e.g., FIGS. 3a and 3c), the seal 72 can withstand sudden changes in pressure, particularly from a pressurized state in which the gas is at cartridge pressure to a depressurized state at atmospheric pressure under conditions of sudden decompression. Sudden decompression, as used in the present specification and appended claims, means very rapid decompression in the instant after the push button or lever is activated to release the gas, typically occurring in less than a second or a fraction of a second, and includes explosive decompression in which the gas release occurs typically in less than about a half second.

Unlike other prior seals used in medical applications, the present seals are adapted to be used with the gas cartridge 64. Seals utilized with prior devices operating from built-in low-pressure gas systems employed in medical facilities lack the physical qualities needed to perform effectively with high-pressure gas systems such as removable pressurized gas cartridges. When using the gas cartridge 64, particularly when using carbon dioxide gas at 5.8 MPa or greater pressure, the contents of the cylinder include liquid carbon dioxide that may directly contact the seal during operation. The seal 72 is designed to operate effectively when contacting liquid carbon dioxide, which can reach temperatures as low as −50° C. as the pressure in the gas cartridge decreases. Additionally, the seal 72 is designed to operate effectively as the gas pressure in the cylinder 68 is released causing a sudden drop in gas pressure from 4 MPa or greater to ambient air pressure in the cylinder 68 around the seal 72. For example, the cartridge pressure, for particular embodiments discussed above, is 4 MPa (40 bar) or greater. Alternatively, the gas pressure is greater than 5 MPa (50 bar). In yet another alternative, the gas is about 6 MPa (60 bar). Typically, the atmospheric pressure is about 0.1 MPa (1 bar), but may be higher or lower, varying by particular location and weather conditions, such as 0.075 MPa (0.75 bar), 0.08 MPa (0.8 bar), 0.09 MPa (0.9 bar), 0.11 MPa (1.1 bar), or other pressures. The sudden drop in pressure may be from, for example, from more than 4 MPa to less than 0.11 MPa, or from 6 MPa to 0.75 MPa, or from 5.8 MPa to 0.1 MPa, or from 5 MPa to 1.0, or any combination of gas cartridge pressure to atmosphere pressure.

Accordingly, the present seals are suitable to withstand use in medical devices powered at least in part by high-pressure gases. Such seals must reflect particular qualities in this regard. For example, some seals herein can exhibit substantially stable performance (e.g., resist failure or breakage, resist leakage of gas, remain in place, avoid restricting movement of parts in contact, have a substantially predictable or indefinite working lifetime) under a variety of changing temperatures. Medical devices are typically sterilized, requiring a resistance to sterilization methods including exposure to high temperatures In particular embodiments, the seal provides substantially stable performance above 100° Celsius, and in alternative embodiments above 110° Celsius, and in other embodiments above 130° Celsius. Additionally, the present seals can maintain their performance when wet or in high-humidity environments (e.g., a water vapor atmosphere). These seals can also be capable of providing substantially stable performance when exposed to low temperatures, particularly when compressed gas is vented. In embodiments, cartridges containing high-pressure liquid of a substance that is gaseous at "room temperature" (e.g., 20 degrees Celsius) are employed. In such embodiments, the seals can withstand temperatures similar to those at which the gas is liquid. In particular embodiments, the seals provide substantially stable performance below −5° Celsius, and in alternative embodiments below −10° Celsius, and in other embodiments below −50° Celsius. To fully resist a sudden drop (or increase) in pressure, the seals can withstand low temperatures, high temperatures, and sudden shifts therebetween.

The present seals have low porosity. Low porosity inhibits high-pressure gases or liquids from saturating pores within the seal to avoid fissuring or breaking the seal. In embodiments, high-pressure carbon dioxide can be employed from disposable cartridges. A low porosity can prevent the carbon dioxide from saturating the seal's pores, which could rupture the seal changes from liquid to gas as gas pressure decreases during cartridge discharge, or as the gas expands thereafter.

In another example, seals herein can be resistant to solvents and/or resist reaction with particular substances. For example, liquid carbon dioxide has a solvent effect. When used in conjunction with liquid carbon dioxide cartridges, the present seals can at least resist solvents of this strength. In another example, seals can retain their qualities and exhibit stable performance in or after contact with lubricants.

Further, the present seals can have a hardness that facilitates ready integration in various systems, including with moving parts, such that they are not prone to failure by friction with the other moving parts, both at low and high pressure. Various materials that comprise at least a portion of a seal herein can have hardness measurements described by the International Rubber Hardness Degree scale. In an example, the seal has a hardness between 70 and 90 as measured according to the International Rubber Hardness Degree scale. In one embodiment, the seal includes a hardness of 80 measured according to the International Rubber Hardness Degree scale.

Seals herein can move with moving parts. In embodiments, a seal can be configured to move with a piston, rotate with a ball, move about a joint, et cetera. The seal can undergo various combinations of translation and rotation, or be translated or rotated as desired with a component to which the seal is attached or operating in conjunction with.

Seals with these qualities are not known to be available in the marketplace. Seals herein can meet such design requirements by comprising, at least in part, particular materials. In embodiments, copolymers (and/or other composite materials) as utilized herein can include one or more of hexafluorpropylene, tetrafluorethylene, vinyldienfluoride, and/or carbon black. In one or more embodiments, the seal includes a fluor terpolymer having not more than 30% hexafluorpropylene, not more than 30% tetrafluorethylene, not more than 15% vinyldienfluoride, and not more than 80% carbon black. In one or more alternative or complementary embodiments, the seal can be constructed of a fluor terpolymer comprised of not less than 10% hexafluorpropylene, not less than 10% tetrafluorethylene, not less than 1% vinyldienfluoride, and not less than 30% carbon black. In embodiments, these portions can be combined in various alternative arrangements whereby the proportions of materials fall into the range provided in one or more embodiments (e.g., not more than 30% hexafluorpropylene and not less than 10% tetrafluorethylene). In one embodiment, the seal includes, 20% hexafluorpropylene, 20% tetrafluorethylene, 5% vinyldienfluoride, and 55% carbon black.

The present seal 72 is used, for example, to prevent gas in the locking device 44 from escaping between piston 70 and cylinder 68.

Seals herein can be manufactured through the use of materials as described and meeting at least a portion of the aforementioned design specifications. In particular, a method for making a seal for use in high pressure gas medical systems can comprise receiving a low-porosity material having a resistance to a sudden drop in gas pressure from a high pressure of more than 4 MPa to a low pressure of less than 0.11 MPa, the material further having substantially stable performance at pressures between the high pressure and the low pressure, the material further having substantially stable performance below −10° Celsius, and the material having substantially stable performance above 110° Celsius. The method can further comprise forming a seal from the received material.

First arm 14 and second arm 16 each have a respective swivel heads cooperating with a respective piston as described above for support arms swivel head 46 and support arm piston 70. Push button 36 (FIG. 2) is used to release first arm 14 and a second push button 86 is used to release second arm 16.

Figure 4A:
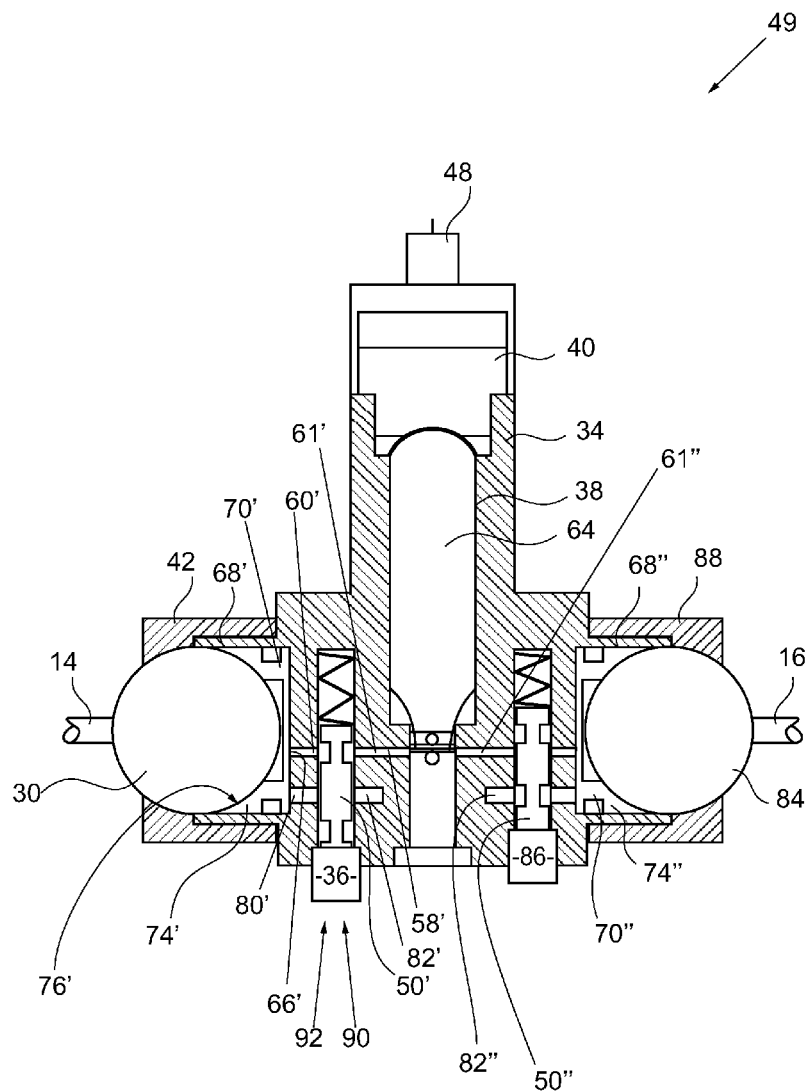
FIG. 4a is a first front cross sectional view of an alternative embodiment of a lockable joint assembly according to the present invention.

FIG. 4a shows a cross section according to plane B of FIG. 2 for a second embodiment of the lockable joint assembly 49. In FIG. 4a push button 36 and second push button 86 are located at the downside of main body 34. This embodiment is chosen to ease the understanding of the mechanism. However, the embodiment shown in FIG. 2 has a respective structure. As shown in FIG. 4a, second arm 16 has a second swivel head 84 that is received in a second socket 88.

FIG. 4a also shows a locking device 90 for first arm 14, having a piston 70', the gas cartridge 64, and an actuating device 92. The actuating device 92 comprises push button 36 and valve member 50'. To avoid repetitions, similar elements as described above are referenced with like reference numerals having a slash added. For example, cylinder 68' has the same features as cylinder 68. In FIG. 4a, push button 36 is in its locking position with cylinder 68' in gas communication only with gas cartridge 64 and push button 86 is in its release position with cylinder 68" in gas communication only with the ambient air.

Figure 4B:
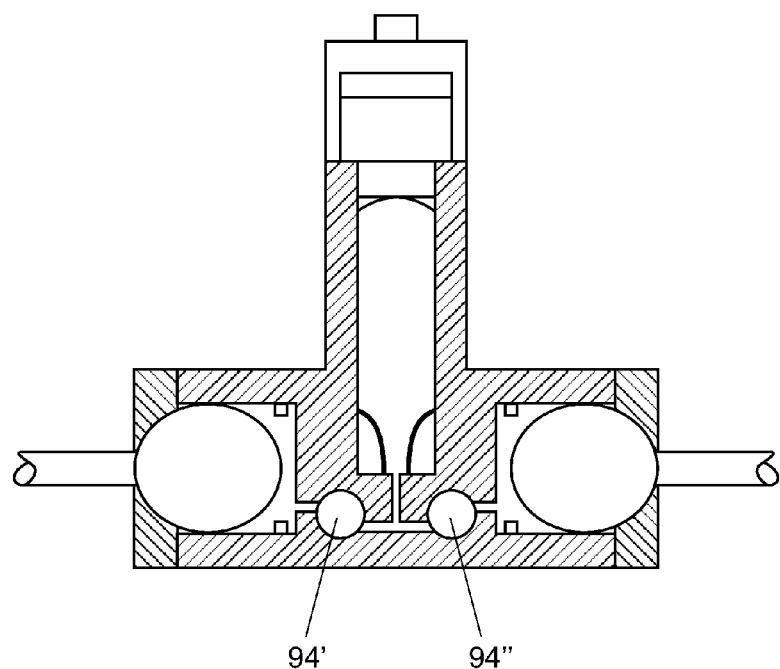

FIG. 4b shows at a different level compared to FIG. 4a, i.e. with respect to a plane C that is parallel to plane B, but moved away from support arm 28 (see FIG. 2). In FIG. 4b, two exhaust openings 94', 94" can be seen. Exhaust openings 94', 94" are in gas communication with second outlet channels 82', 82" (see FIG. 4a), respectively.

Figure 5C:
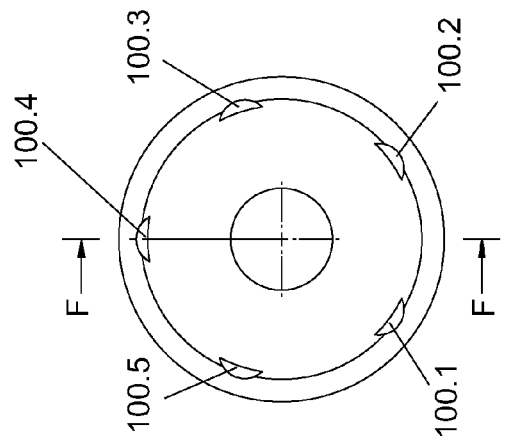
FIG. 5c is a front view of the piston depicted in FIGS. 5a and 5b.
Figure 5B:
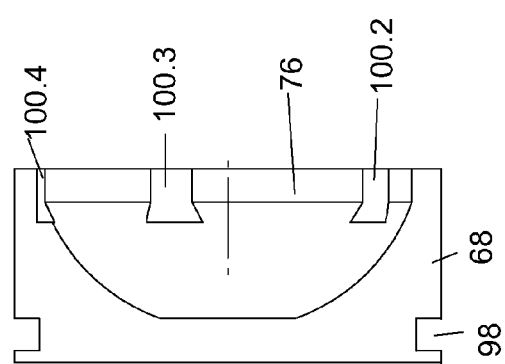
Figure 5A:
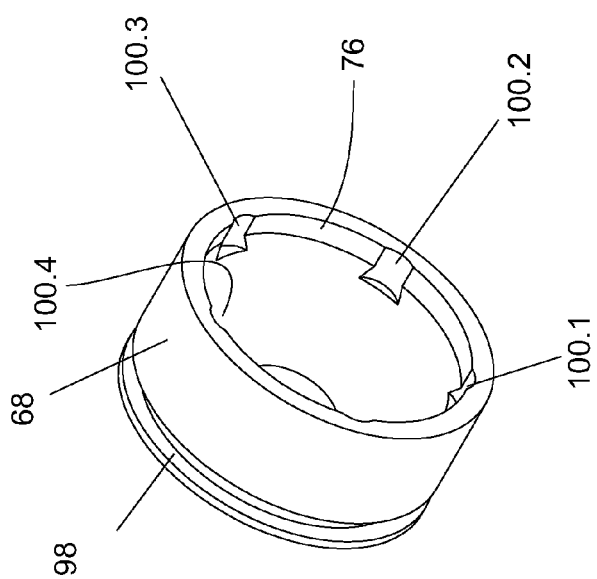
FIG. 5a is a perspective view of the piston comprising the fixing element.

FIG. 5a shows cylinder 68 having an annular recess 98 for seal 72 (not shown). Cylinder 68 has four clearances 100.1, 100.2, 100.3, 100.4. Due to these clearances, fixing element contact area 76 is segmented (see FIG. 3b).

FIG. 5b shows a cross section of cylinder 68 and FIG. 5c shows a front view. FIG. 5b is a cut along line F-F of FIG. 5c.

Figure 6B:
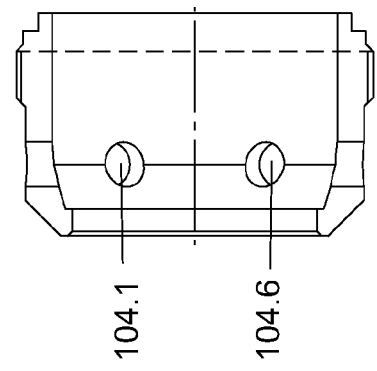
Figure 6D:
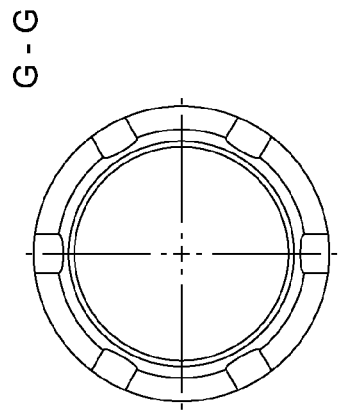
FIG. 6d a cut along C-C of FIG. 6c.
Figure 6A:
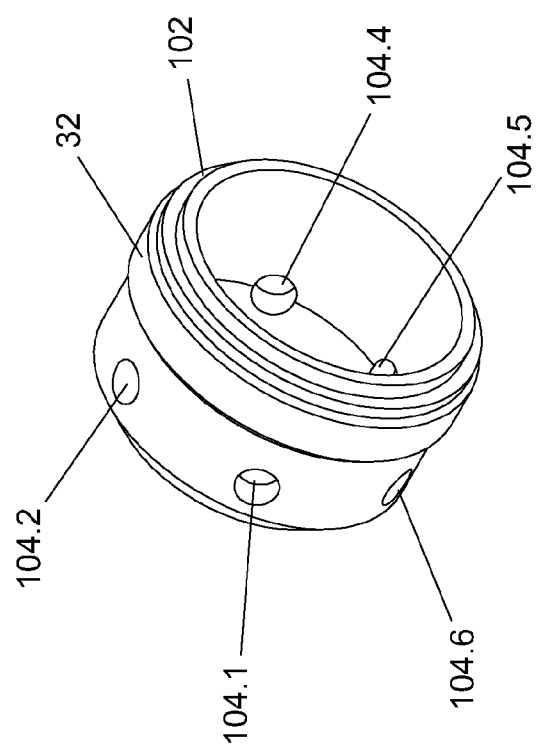
FIG. 6a a socket for a lockable joint according to the invention in a perspective view.

FIG. 6a shows a perspective view of socket 32. Second socket 88 and support arm socket 42 have the identical shape. Socket 32 has a thread 102 for threaded engagement with a respective thread in main body 34 (see FIG. 3a). Socket 32 has a plurality of bores 104.1, 104.2, . . . that allow liquids or gases to reach those parts of swivel head 30, that are captured within socket 32. This is particularly advantageous for cleaning and disinfecting.

Figure 6C:
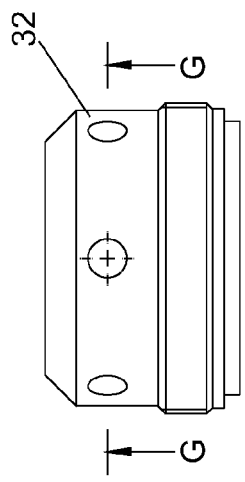
FIG. 6c is a side view of the socket of FIGS. 6a and 6b.

FIG. 6b shows a cross section of socket 32, FIG. 6c is a side view, and FIG. 6d is a cut along line G-G of FIG. 6c.

Figure 7:
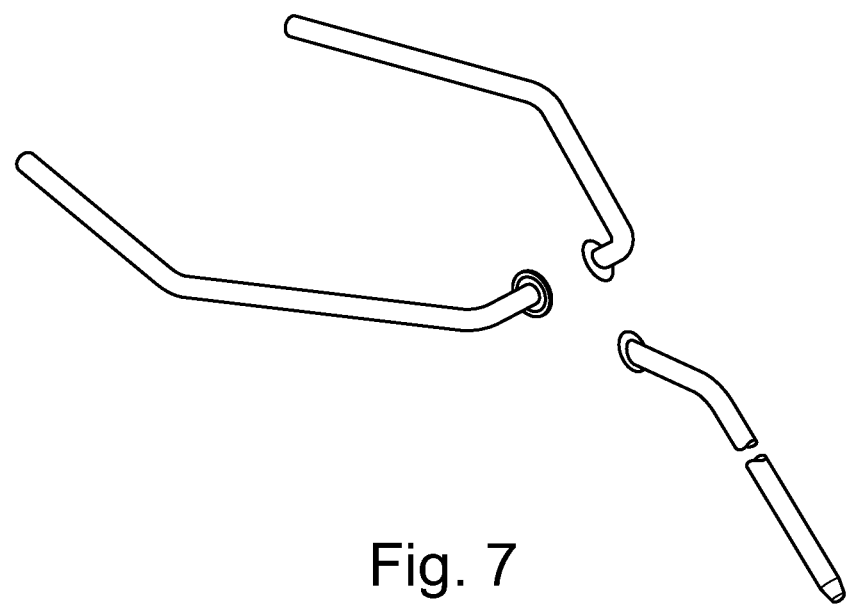
FIG. 7 is a perspective view of a support arm and two frame arms of a surgical retractor frame in accordance with the invention.

FIG. 7 shows first arm 14, second arm 16, and support arm 28 in a prospective view.

Figure 8:
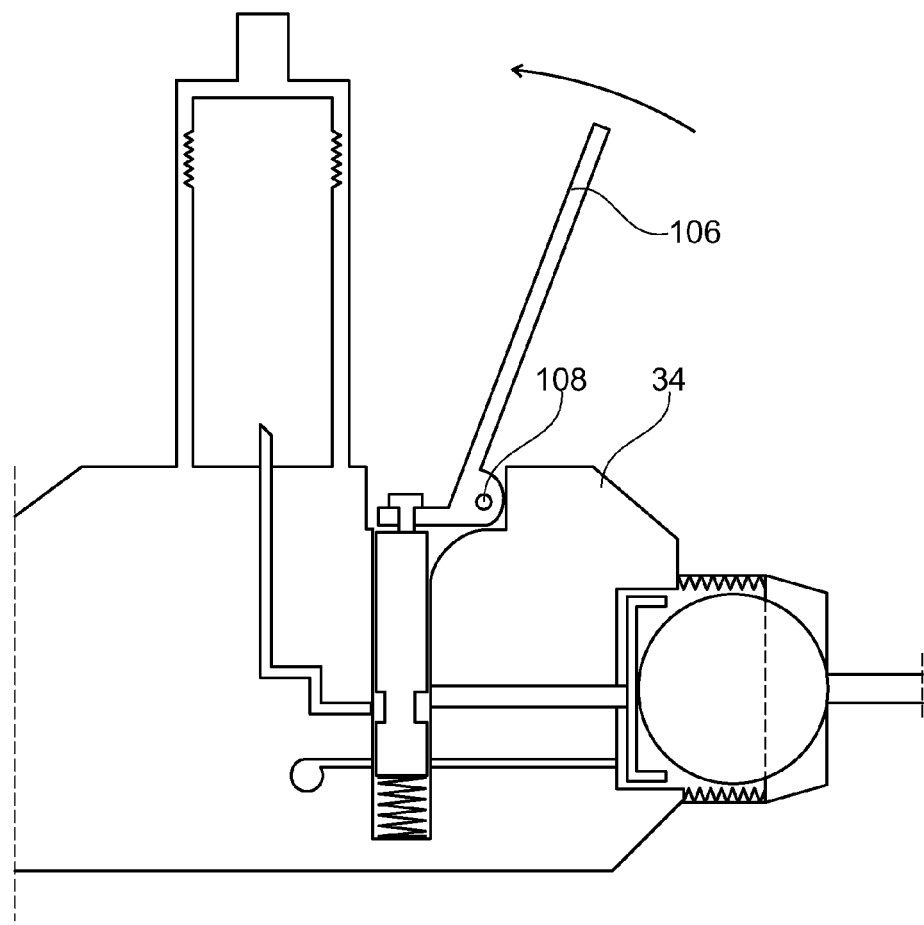
FIG. 8 is a cross sectional view of another embodiment of a lockable joint in accordance with the invention.

FIG. 8 shows an alternative embodiment of an inventive lockable joint 43. For the sake of easy handling, a push button has been replaced by a lever 106 that is pivotably connected to main body 34 via a hinge 108.

Figure 9:
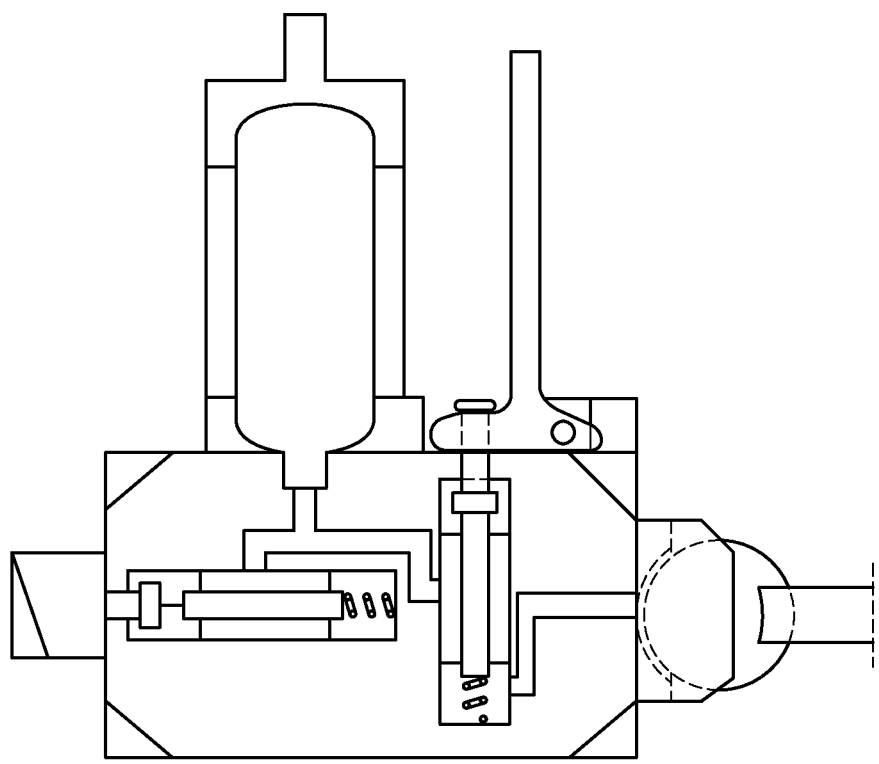
FIG. 9 is a cross sectional view of still another embodiment of a lockable joint in accordance with the invention.

FIG. 9 shows an embodiment of an inventive lockable joint assembly 49 in a cross sectional view.

Referring to FIGS. 3a and 4a, compressed gas cylinder 64 may be located within control hand piece 34. Screw 40 forces compressed gas cylinder 64 against a hollow piercing member (not shown) that pierces a malleable seal of the gas cartridge 64 and connects the interior of compressed gas cylinder 64 with gas conduits within or coupled to control hand piece 34. Gas flow is then controlled by push buttons or other valve actuators to selectively apply or release pressure on pistons to lock or unlock the ball joints.

The present invention is described herein, using the example of a surgical retractor frame. It should be understood that there are many other applications of the present invention both in a surgical and a non-surgical setting, both within and outside of health care where it is desirable to fix or lock articulated joints such as but not limited to ball joints. It should be understood that the invention maybe applied to other devices such as: Articulating arm joint holding devices including but not limited to: endoscopic scopeholder; endoscopic retractor holder, fan and other; endoscopic instrument/device holder; surgical screen holder; leg stirrups; and vertical/table post clamp devices. Articulating clamps/joints used in patient positioning; Wilson frame for spinal applications; OR tables; adjustment and locking mechanisms; orthopedic traction devices; and bone cement applicator.

REFERENCE NUMERALS 10 surgical retractor system
12 surgical retractor
14 first arm
16 second arm
18 surgical retractor frame
20 anchor element
22 coupling anchor
24 clamping rod
26 anchor element joint
28 support arm
30 swivel head
32 socket
34 main body
36 push button
38 gas cartridge retainer
40 gas cartridge chamber screw
42 support arm socket
43 lockable joint
44 support arm locking device
46 support arm swivel head
48 support arm push button
49 lockable joint assembly
50 support arm valve member
52 bore
54 spring
56 annular recess
58 first gas channel
60 second gas channel
61 gas duct
62 gas cartridge outlet opening
64 carbon dioxide cartridge
66 cylinder inlet opening 68 cylinder
70 support arm piston
72 seal
74 fixing section
76 fixing element contact area
78 second annular recess
80 first outlet channel
82 second outlet channel
84 second swivel head
86 second push button
88 second socket
90 locking device
92 actuating device
94,96 exhaust opening
98 annular recess
100 clearance
102 thread
104 bore
106 lever
108 hinge
A, B, C, E plane
d contact area outer diameter
$D_{piston}$ piston diameter
$D_{sh}$ swivel head outer diameter
$D_{ca}$ contact area outer diameter
L longitudinal axis
p gas pressure
$\vec{P}$ piston working direction
s stroke
V Volume
w ring width

What is claimed is:

1. A lockable ball-and-socket joint, comprising:
a first arm having a swivel head,
a socket, the swivel head being pivotably mounted within the socket, and
a locking device arranged for locking the swivel head with respect to the socket, the locking device having:
a cylinder within the socket,
a piston movably mounted within the socket, and comprising a fixing element for pressing against the swivel head,
a high-pressure seal providing a gas seal between the piston and the cylinder, the seal made at least in part of a material being resistant to a sudden drop in gas pressure from a high pressure of more than 4 MPa to a low pressure of less than 0.11 MPa, the material further having substantially stable performance at pressures between the low pressure and the high pressure, and the material further having low porosity,
a pressure gas source comprising a gas cartridge operatively coupled to the locking device and having an internal pressure of more than 4 MPa, and
an actuating device arranged for selectively connecting and disconnecting the piston from the pressure gas source.

2. The lockable joint according to claim 1,
the gas cartridge containing less than 50 g of gas and having a gas cartridge outlet opening,
the cylinder having a cylinder inlet opening,
the cylinder and the gas cartridge being in gas communication via a gas duct between the gas cartridge outlet opening and the cylinder inlet opening,
the gas duct having a volume of less than 1000 mm3,
the fixing element comprising a fixing section for pressing against the swivel head, the fixing section being located opposite the cylinder inlet opening.

3. The lockable joint according to claim 1, wherein the gas cartridge contains one selected from the group consisting of carbon dioxide, pressurized air, pressurized nitrogen, pressurized nitrous oxide, or a mixture of any combination thereof.

4. The lockable joint according to claim 3, the gas cartridge being a carbon dioxide cartridge containing liquid carbon dioxide.

5. The lockable joint according to claim 4, the carbon dioxide cartridge containing sterile carbon dioxide.

6. The lockable joint according to claim 1, the piston and the fixing element being connected, such that moving the piston in a piston working direction leads to a movement of the fixing element in a fixing element working direction, the piston working direction being parallel to the fixing element working direction.

7. The lockable joint according to claim 6, the piston and the fixing element being directly coupled, such that moving the piston by a predetermined distance leads to a movement of the fixing element by the same predetermined distance.

8. The lockable joint according to claim 1, the piston and the fixing element being directly coupled, such that moving the piston by a predetermined distance leads to a movement of the fixing element by the same predetermined distance.

9. The lockable joint according to claim 1, comprising a gas cartridge retainer for exchangeably receiving the gas cartridge.

10. The lockable joint according to claim 1, the fixing element being arranged for pressing against the swivel head via a fixing element contact area, the fixing element contact area being ring-shaped having a ring width of less than 1 mm.

11. The lockable joint according to claim 10, the fixing element being arranged for frictional locking between the fixing element and the swivel head.

12. The lockable joint according to claim 10, the fixing element contact area being segmented.

13. The lockable joint according to claim 12, the swivel head having a swivel head outer diameter and contacting the fixing element in a ring-shaped swivel head contact area, and the ring-shaped contact area having a contact area outer diameter that is larger than 0.94 times the swivel head outer diameter.

14. The lockable joint according to claim 1, the first arm having an arm longitudinal axis and a contact area outer diameter and a plane perpendicular to the arm longitudinal axis forming a substantially constant effective angle of less than 20°.

15. The lockable joint according to claim 14, the effective angle being larger than 1°.

16. The lockable joint according to claim 1, the piston having a stroke of less than 2 mm.

17. The lockable joint according to claim 1, the piston having a piston diameter of more than 20 mm.

18. The lockable joint of claim 1, the seal material being a fluor terpolymer comprising hexafluorpropylene, tetrafluorethylene, vinyldienfluoride, and carbon black.

19. The lockable joint of claim 1, wherein the seal material is adapted to withstand exposure to liquid carbon dioxide.

20. The lockable joint of claim 1, wherein the seal material is adapted to withstand more than 130° Celsius in a water vapor atmosphere.

21. The lockable joint of claim 1, wherein the seal material has a hardness of 70-90 according to the International Rubber Hardness Degree scale.

22. The lockable joint of claim 1, wherein the seal material is resistant to a sudden drop in gas pressure from more than 6 MPa to less than 0.1 MPa.

* * * * *